United States Patent [19]

Mason et al.

[11] Patent Number: 4,940,581

[45] Date of Patent: Jul. 10, 1990

[54] PLATELET CYROPRESERVATION

[75] Inventors: James M. Mason; David D. Pifer, both of Memphis, Tenn.

[73] Assignee: The University of Tennessee Research Corporation, Knoxville, Tenn.

[21] Appl. No.: 233,999

[22] Filed: Aug. 15, 1988

Related U.S. Application Data

[63] Continuation-in-part of Ser. No. 924,964, Oct. 30, 1986, Pat. No. 4,764,463.

[51] Int. Cl.$^5$ ............................................... A61K 35/14
[52] U.S. Cl. ........................................ 424/532; 435/2
[58] Field of Search ............................ 435/2; 424/101

[56] References Cited

U.S. PATENT DOCUMENTS

| | | |
|---|---|---|
| 3,296,091 | 1/1967 | Beal et al. . |
| 3,629,071 | 12/1971 | Sekhar . |
| 3,729,947 | 5/1973 | Higuchi . |
| 3,996,103 | 12/1976 | Sekhar . |
| 4,033,816 | 7/1977 | Sekhar . |
| 4,059,967 | 11/1977 | Rowe . |
| 4,110,161 | 8/1978 | Sekhar . |
| 4,251,995 | 2/1981 | Pert . |
| 4,303,671 | 12/1981 | Fitzpatrick . |
| 4,365,629 | 12/1982 | Pert et al. . |
| 4,390,619 | 6/1983 | Harmening-Pittiglio . |
| 4,476,221 | 10/1984 | Kane et al. . |
| 4,558,142 | 12/1985 | Holland . |
| 4,764,463 | 8/1988 | Mason et al. ........................ 435/2 |

OTHER PUBLICATIONS

Blackwell et al–Chem. Abst., vol. 97 (1982), p. 175, 888a.

G. H. R. Rao et al, Influence of pH on the Prostacyclin (PGI$_2$) Mediated Inhibition of Platelet Function, Prostaglandins and Medicine 4:263–273, 1980.

*Primary Examiner*—Sam Rosen
*Attorney, Agent, or Firm*—Luedeka, Hodges & Neely

[57] ABSTRACT

A method for preserving blood platelets by freezing the platelets in contact with a cryoprotectant solution containing a sufficient quantity of prostacyclin for the substantially complete inhibition of platelet function and having a pH which promotes the preservation of the platelets and reconstituting the platelets for infusion.

5 Claims, No Drawings

PLATELET CYROPRESERVATION

This application is a continuation-in-part of our copending application Ser. No. 06/924,964, filed Oct. 30, 1986, now U.S. Pat. No. 4,764,463.

The present invention relates to the preservation of blood platelets for subsequent clinical use and more particularly relates to a method for platelet cryopreservation including a "one-step" dilution of the thawed platelets for infusion.

Blood platelets, which are necessary for the clotting of blood, are desired for transfusions to patients with both congenital and drug-induced clotting deficiencies caused by low platelet counts. While platelets are easily separated from whole blood, loss of the hemostatic function over time generally limits the room temperature storage (22° C. optimum temperature) of platelets to a matter of days. Platelet suspensions suitable for transfusions are often in short supply.

To achieve long term storage of blood platelets, various cryopreservation methods have been developed. One such method employs dimethyl sulfoxide (DMSO) as a cryoprotectant in a slow freezing process. However, the toxicity of DMSO requires that the DMSO be removed from thawed platelets prior to use. To eliminate the need for additional preparation of the thawed platelets, platelets have been frozen in acidic glycerol-glucose solutions. While these methods enable the direct transfusion of the thawed platelets, the quantity and quality of the recovered platelets is not sufficiently high for platelet cryopreservation to be widely used.

Frozen platelets heretofore have been reconstituted for infusion employing a three-step procedure such as outlined in our copending application Ser. No. 06/924,964. Specifically, in preparing platelets for freezing, the platelets are concentrated in a medium to provide platelet-rich plasma (PRP). The PRP is frozen, preferably rapidly; e.g., at a cooling rate of greater than about $-20°$ C. per minute. When the platelets are needed for infusion into a patient, the frozen PRP is commonly thawed by placing the bag of frozen PRP in water at about room temperature; e.g. 22° C., with mild agitation of the water. After thawing the PRP must be diluted to a concentration suitable for infusion into the patient. This reconstitution procedure has heretofore involved a "three-step" dilution. In the first step, for example, a volume of diluent equal to the volume of the concentrate is added over a three-minute period and the platelets are allowed to equilibrate for 15 minutes at room temperature. In the second step the volume of diluent is doubled, again being added to the product of the first step over a three-minute time period and allowed to equilibrate at room temperature for 10 minutes. The third step is identical to the second step. After all diluent has been added, the concentration is allowed to equilibrate for an additional period of time, e.g., 30 minutes to ensure full reconstitution of the platelets. This extended-time reconstitution procedure has almost universally been deemed necessary to prevent damage to the platelets and/or to ensure that they return as nearly as possible to their original morphology and biological viability.

It is accordingly an object of the present invention to provide a method for platelet cryopreservation and for the reconstitution of the thawed concentrate for infusion. It is another object of the method to provide a platelet preparation upon thawing which can be safely used for platelet transfusions without additional preparation. It is another object to provide an improved method of cryopreservation of platelets including a one-step procedure for reconstituting the concentrate for infusion which is relatively time-saving. It is another object to provide a method for platelet cryopreservation which is suitable for routine use by blood bank technicians.

In applicant's copending application, Ser. No. 06/924,964, there is described a novel method for preserving platelets for extended periods by freezing the platelets in contact with a cryoprotectant solution containing sufficient prostacyclin to substantially completely inhibit platelet function and having a pH which promotes the preservation of the platelets. The frozen platelet preparation thus prepared may be stored for extended periods and, upon thawing, contains a high yield of functioning platelets and can be safely transfused to humans.

In the course of working with the frozen platelet preparations produced by the method disclosed in such copending application, applicants were surprised to find that the resultant platelet preparation, upon thawing, could be reconstituted in a single dilution step in which the full volume of diluent was added over a period of 5 minutes and incubated at 37° C. for 15 minutes. Notably the post-thaw yield, morphology scores and aggregability of the platelets prepared in the single dilution step were not significantly different from the same properties of autologous platelets diluted using the 3-step method of the prior art. Accordingly, the present method discovered by the inventors provides a timesaving of at least about one hour in the dilution step without loss of platelet recovery, morphology or function.

It has been observed that platelets shrink when frozen and swell when reconstituted in the presence of a diluent such as platelet-poor plasma. In the diluent, the platelets reshape into their original disc form. This process has been observed and monitored. For example, exposing the reconstituted platelets in a bright light reveals "swirling" as the platelets regain their original disc shape. Employing the prior art methods of freezing and reconstitution, the time that is required for the platelets to regain their disc shape has heretofore been on the order of 1–2 hours.

One theory regarding the restoration of the platelets to their disc shape calls attention to the fact that platelets depend upon a marginal micro-tubular bundle to maintain their disc shape. This micro-tubular structure can be disrupted by osmotic shock as in the reconstitution step, requiring restructuring of the micro-tubular system as well as restoring the fluid volume and electrolyte concentration to normal. This micro-tubular system also can be disrupted by cold. Thus, heretofore, it has been the common practice to be most careful in the procedures involved in reconstituting the platelets to insure that a maximum number of the platelets return to their original morphology and that the platelets are subjected to a minimum of possible adverse conditions, e.g. osmotic shock.

The present single step dilution procedure is not possible in the absence of prostacyclin in the concentrate. It is not known with certainty, but the present inventors postulate that the presence of prostacyclin during the freezing and dilution procedures in some way inhibits the heretofore noted deleterious effects upon the morphology of the platelets due to freezing and thawing, hence enhances the inherent ability of the platelets to reassume their original morphology and therefore their original function.

Prostacyclin (PGI2) is a member of a class of compounds referred to as prostaglandins which are associated with the regulation of smooth muscle activity, lipid metabolism, and reproductive physiology. Prostacyclin is a potent stimulater of adenylate cyclase, which results in increased cyclic AMP and inhibition of platelet function. Under acidic conditions and in weakly basic solutions such as normal blood plasma, prostacyclin spontaneously decomposes with a half-life of about 15 minutes at pH 7.4.

During freezing in accordance with the invention disclosed in copending application Ser. No. 06/924,964, and in the present method it is necessary to maintain the level of the prostacyclin in the cryoprotectant solution at a level sufficient for the substantially complete inhibition of platelet function. Because of decomposition of prostacyclin in the cryoprotectant solution, the quantity of prostacyclin must be sufficient initially so that a sufficient quantity remains throughout the freezing process. Preferably, a minimum necessary amount is employed which produces inhibition since an excess may interfere with the aggregation after transfusion. A suitable amount has been found to be approximately 130 ug per platelets in a blood unit in a cryoprotectant at pH 7.4. The amount is variable depending on the composition and pH of the cryoprotectant solution. Although unnecessary. It is believed to be possible to use prostacyclin stabilizers such as albumin in the cryoprotectant solution so long as they do not affect the activity of the platelets upon transfusion or otherwise affect the preservation of the platelets.

The pH of the cryoprotectant solution during freezing must be maintained at a level which facilitates the preservation of the platelets. Thus, the pH must be limited to below about 8.0 even though prostacyclin is unstable at low pH levels. However, the rapid decomposition of prostacyclin at low pH makes it impractical to use a pH of less than about 7.0. Because the optimum environment for preservation is achieved when the pH approximates the physiological pH of blood plasma, it is preferable to employ a cryoprotectant solution having a pH of between about 7.2 and about 7.6.

The cryoprotectant solution employed is an aqueous solution with an osmolarity value consistent with platelet preservation and containing constituents for promoting the preservation of the platelets during the freezing process while also being compatible with prostacyclin. In addition, it is desirable for the cryoprotectant solution to permit the direct transfusion of thawed platelets with no preparation other than resuspension in plasma. The preferred cryoprotectant solution is a glycerol-glucose saline solution such as the solution disclosed in U.S. Pat. No. 4,059,967, the disclosure of which is incorporated herein by reference. It is desirable to use such a cryoprotectant solution with a pH in accordance with the present invention having between about 4 and about 7 weight percent glycerol and between about 2 and about 6 weight percent glucose.

In order to achieve the desired pH of the cryoprotectant solution, it is generally necessary to employ a compound which functions as a pH buffer which is otherwise compatible with the platelets and prostacyclin and which preferably is suitable for direct transfusion of the platelets to human subjects. In the preferred glycerol-glucose cryoprotectant solution, a suitable buffer is sodium citrate. It is desirable to maintain the concentration of sodium citrate at a level which does not adversely effect the osmolarity of the cryoprotectant.

Freezing of the platelets is preferably achieved by containing the platelets in the cryoprotectant solution in plastic bags and forming the bags into a generally planar configuration so that the heat transferred during freezing is generally consistent throughout the cryoprotectant solution. It is particularly desirable to employ the controlled freezing method disclosed in U.S. Pat. No. 4,251,995, the disclosure of which is incorporated herein by reference. The freezing bags are placed in a cassette with two corrugated cardboard sheets adjacent the freezing bag and two metal plates in contact with the cardboard. The cassette is frozen by immersing in liquid nitrogen with the resulting freezing rate being about −20° C. to about −30° C. per minute.

Before freezing of the platelets in contact with the cryoprotectant solution according to the present invention, it is preferable to prepare a platelet concentrate in which the platelets from one unit of blood are suspended in about 5 to 15 ml of liquid. A suitable platelet concentrate can be prepared from platelet rich plasma which is separated by centrifugation from a unit of blood which has been collected into an anti-coagulant solution such as CPDA-1 (Citrate-Phosphate-Dextrose-Adenine). The concentrate is prepared from the platelet rich plasma by further centrifugation under conditions which prevent platelet aggregation.

In the preferred form of the invention, aggregation of the platelets during preparation of the concentrate is prevented by the presence of sufficient prostacyclin in the platelet rich plasma to substantially inhibit platelet function. Since the prostacyclin inhibits platelet function at the normal pH of the plasma, there is no need to adjust the pH to approximately 6.5 as is commonly done before centrifugation to produce the concentrate. The concentrate is suitable for freezing in the cryoprotectant without any large adjustment of the pH before freezing which could create an undesirable increase in osmolarity in the cryoprotectant solution. It has been found that a suitable amount of prostacyclin in the platelet rich plasma to achieve this result is 70 ug per platelets in one unit of blood which can be achieved by direct addition of prostacyclin to the platelet rich plasma.

Formation of the platelet concentrate is advantageously carried out by resuspending the platelets from one unit of blood in a small quantity of the supernatant plasma, e.g., 5 to 15 ml. The cryoprotectant solution is formed by adding to the concentrate, the prostacyclin and a concentrated solution having the constituents of the cryoprotectant solution, which when mixed with the plasma in the concentrate, produces the desired cryoprotectant solution. For example, a concentrate containing approximately 8% glucose, 10% glycerol, and 0.04M sodium citrate can be mixed with equal volumes of the platelet concentrate to produce the cryoprotectant solution. The prostacyclin to be present in the cryoprotectant solution is preferably added to the platelet concentrate before the cryoprotectant solution is formed but also can be present in the concentrated solution provided that it is added immediately before that solution is mixed with the platelet concentrate. Thus, in the preferred form of the invention, the platelets are maintained in the presence of at least some prostacyclin prior to and during freezing and reconstitution.

To prepare the frozen platelets for use, the platelets are merely thawed, preferably quickly. This is suitably accomplished, for example, by immersing the same bags in which they were frozen in a water bath at room temperature (20° to 25° C.). In accordance with the present invention, the platelets are reconstituted by resuspending the platelets in a plasma or synthetic plasma diluent in a single-step procedure. This suspension is suitable for direct transfusion. The prostacyclin is labile in the plasma and the inhibition of platelet function due to the prostacyclin will essentially disappear upon transfusion.

The invention can be more readily understood and appreciated when reference is made to the following example which illustrates an embodiment of the invention without any intent to limit the invention to the embodiment disclosed.

EXAMPLE

PREPARATION OF PLATELET CONCENTRATE

Platelets were prepared from eighteen fresh units of whole blood collected in plastic bags containing CPDA-1 anticoagulant and the platelets from each unit were frozen in accordance with the following procedures within 6 hours of collection. The units were centrifuged in a Sorvall RC-3 centrifuge for 10 minutes at 1800 RPM and 22° C. The platelet-rich plasma (PRP) was removed to a satellite bag and approximately 70 ug of prostacyclin (UpJohn, Kalamazoo, Mich.) were added. The PRP was then centrifuged for 10 minutes at 4100 RPM and 22° C. Most of the supernatant platelet-poor plasma (PPP) was removed, leaving a concentrate volume between 7 and 15 ml. The PPP was frozen for use as a diluent when the platelets were thawed.

FREEZING PROCEDURE

An additional 30 ug of prostacyclin were added and the platelets were manually resuspended to produce a platelet concentrate. A concentrated cryoprotectant solution was prepared by dissolving 80 g of glucose, 100 ml of glycerol, and 11.75 g sodium citrate $\cdot 2H_2O$ in a total volume of 1 liter using sterile water. The platelet concentrate was transferred to a polyolefin freezing bag sold under the trademark PHARMAFLEX by Pharmachem, Bethlehem, Pa. The outer plastic bag in which the freezing bag was shipped was reserved and used to hold the freezing cassette assembly during the freezing process. An equal volume of the concentrated cryoprotectant solution was added resulting in a final volume of 15-30 ml to be frozen. All air was expressed and the bag was sealed.

Each platelet concentrate bag was placed between hinged sheets of corrugated cardboard (single-wall, bursting strength 19.4 $kg/cm^2$, C flute obtained from Longview Fibre Co., Amsterdam, N.Y.) with the ports away from the hinge. Each sheet measured 13.3 by 15.2 cm. Between the cardboard sheets, the concentrate bags assumed a V-shaped configuration, the geometry of which assures that the concentrate will freeze from the bottom up, with no pockets of liquid trapped within the bag. The cardboard sheets also served to control the rate of heat transfer to between about $-20°$ C. and about $-30°$ C./minute during freezing and to protect the unit during storage. The cardboard-freezing bag assembly was put between hinged 0.64 cm thick aluminum plates, which served to maintain the V-shaped configuration of the concentrate bag and to moderate heat transfer during freezing. The entire assembly was placed in the plastic shipping bag reserved earlier and allowed to equilibrate at room temperature for 15 minutes. The top of the outer bag was folded twice and the folded edge was pierced by two cup hooks attached to a ½-inch wooden dowel. The outer plastic bag prevents the platelet concentrate bag from coming into direct contact with the liquid nitrogen and prevents the formation of gaseous nitrogen on the aluminum plates, which would alter the rate of freezing by acting as an insulator. The suspension device allowed the freezing cassette to be submerged in the liquid nitrogen while preventing entry of liquid nitrogen into the bag. After 15 minutes in the liquid nitrogen, the outer plastic bag and metal cassette were removed and the concentrate bag and its cardboard protector were transferred to an aluminum holder for storage at $-150°$ C. in the vapor phase of a liquid nitrogen freezer.

THAWING AND RECONSTITUTION

The freezing bag was removed from its cardboard cover and thawed in 22° C. water with minimal agitation. Immediately after thawing, some units were divided into two equal aliquots for reconstitution. One aliquot was prepared using autologous or ABO-compatible PPP reserved during the preparation process as the diluent. A second aliquot was prepared using a synthetic post-thaw diluent (PD) of 0.5 ml destrose in 57 ml of the solution sold under the trademark PLASMALYTE by Travenol, Deerfield, Ill. Other units were reconstituted using PPP only. Reconstitution was accomplished by adding diluent to one of the concentrates in three stages with gentle rocking during addition of diluent and incubations at room temperature between additions. In the first step, a volume of diluent equal to the volume of concentrate was added over a three-minute period and the platelets were allowed to equilibrate for 15 minutes at room temperature. In the second step the volume of diluent added was doubled. The dilution was again done over a three-minute period and was followed by a 10 minute equilibration period. The third step was identical to the second. After all diluent was added, the concentration was allowed to equilibrate for an additional 30 minutes before samples were taken for evaluation of platelet structure and function. The second aliquot was reconstituted in a single step by adding to the concentrate a volume of diluent equal to the total volume of diluent used in the 3-step procedure. This diluent was added to the concentrate over a period of 5 minutes. The diluted platelets were then allowed to incubate at 37° C. for 15 minutes.

PLATELET YIELD AND MORPHOLOGY

Post-thaw yield was calculated by comparing the pre-freeze and post-thaw platelet counts. Pre-freeze counts were performed instrumentally using a Baker 210 platelet analyzer (Baker Diagnostics, Bethlehem, Pa.). Because of reported spurious instrumental counts on thawed platelets, post-thaw counts were performed manually by phase microscopy.

The addition of the diluent in the present method over a five-minute time period has been found to be effective, but it is anticipated that this time period may be shortened to not less than about 3 minutes and may be lengthened considerably, but not preferably, to a much longer time span, e.g. 10-15 minutes. It has been found to be important that the temperature of the concentrate during dilution be raised from the initial 23° C. at thawing to the desired 37° C. for incubation. It appears that the preferred reconstitution of the platelet morphology, and other associated characteristics, occurs at 37° C. (normal body temperature) plus or minus about 0.5° C., hence in the present method it is most important that the temperature of the concentrate and the diluted platelets be closely controlled. In particular, during incubation, the temperature of the platelets should range between about 36.5° C. and 37.5° C. Incubation for longer than 15 minutes has not shown to enhance the characteristics or function of the platelets. Incubation times appreciably less than 15 minutes, however, do not provide adequate time for reconstitution of the platelet morphology to make them suitable for infusion. It is postulated that the contribution of the prostacyclin to the newly discovered ability to reconstitute the platelets drops below its effectiveness level after 15 minutes, which is the half-life of prostacyclin, and the platelets become subject to excessive aggregation.

Changes in platelet morphology were assessed by examining the platelets according to the morphology scoring method of Kuniki et al, Transfusion, Vol. 15, pp. 414-421 (Oct. 1975). Each platelet was classified by shape and assigned a numerical value: 4 points for those platelets which maintained a normal discoid appearance, 2 for those which had undergone a shape change to a spherical form, 1 for those with observable dendritic projections, and 0 points for platelets which had released the contents of their granules and were seen only as greatly enlarged membrane ghosts. The values for the two hundred platelets were totaled and divided by two to give the morphology score for that preparation.

PLATELET AGGREGATION

Platelet aggregation was measured on a Payton Dual Channel Aggregometer, Payton Associates, Inc., Buffalo, N.Y., according to the method of Born, J. Physiol. 168, 178-95 (1963). The count of the platelet concentrates was adjusted to $250-350 \times 10^6$/ul with PPP for aggregation and all other in vitro platelet function studies. Various aggregating agents were added to 0.5 ml of PRP at 37° C. with continuous stirring. Light transmission was measured to determine the degree of aggregation. As aggregates formed, more light was transmitted through the PRP. Aggregating agents, used at final concentrations selected to give maximum aggregation, were: 10 um ADP (Sigma), 55 uM epinephrine (Sigma), 2 ug/ml A23187 (Cal Biochem Behring, San Diego, Calif.), 500 ug/ml arachidonic acid (NuCheck Preparations, Inc., Elysian, Minn.), and 800 nM platelet aggregating factor (PAF, Bachem Feinchemikalien, Bubesdorf, Switzerland). Human fibrinogen, grade L, 95% clottable (Kabi, Stockholm, Sweden) was added to the concentrates reconstituted in PD. In addition to assessing the effect of each agent singly, a synergistic aggregation mechanism was studied by adding first epinephrine, then ADP to the PRP. Aggregation studies were performed at 0, 3, and 5 hours post-thaw for some concentrates to assess the possible effects of PGI2 remaining in the thawed and reconstituted product.

Platelets reconstituted by the time-saving single-step method of the present invention provided platelets that were not significantly different in yield, morphology or function from platelets reconstituted by the prior art 3-step method. The time savings represented by the present method is between about 1 to 2 hours, depending upon the exact protocol followed by a laboratory following the prior art protocol. One other advantage, aside from the economies of the time factor, is the ability to supply reconstituted platelets more quickly in emergency situations. It is felt also that infused platelets at 37° C. are less traumatic to the patient. Still further, the present single step method offers less opportunity for lab error than the multiple step method of the prior art.

What is claimed:

1. In a method for the preservation of blood platelets wherein the platelets are frozen in a concentrated state in the presence of a sufficient quantity of prostacyclin for the substantially complete inhibition of platelet function and subsequently thawed in the presence of prostacyclin and at a pH below about 8, the improved step comprising the substantially continuous addition to said thawed concentrate of a sufficient quantity of a diluent to reduce the concentration of the platelets to that quantity acceptable for infusion, and thereafter incubating said diluted platelets at about 37° C. to permit said platelets to substantially recover their pre-freezing morphology.

2. The method of claim 1 wherein said diluted platelets are incubated for a time period equal to about the half life of prostacyclin.

3. The method of claim 2 wherein said platelets are incubated for about 15 minutes.

4. The method of claim 1 wherein said incubation temperature is maintained between about 36.5° C. and about 37.5° C.

5. The method of claim 1 wherein said substantially continuous addition of diluent continues over a time period of about 5 minutes.

* * * * *